United States Patent [19]

Turbe

[11] Patent Number: 4,662,224
[45] Date of Patent: May 5, 1987

[54] PROCESS AND DEVICE FOR THE AUTOMATIC RECOGNITION AND DETECTION OF DISCONTINUITIES AND IRREGULARITIES IN THE RAILS OF RAILROAD TRACKS

[75] Inventor: Jean-Pierre Turbe, Nanteuil-les-Meaux, France

[73] Assignees: Societe Nationale des Chemins de Fer Francais; Matix Industries, both of Paris, France

[21] Appl. No.: 807,070
[22] PCT Filed: Mar. 22, 1985
[86] PCT No.: PCT/FR85/00057
§ 371 Date: Nov. 22, 1985
§ 102(e) Date: Nov. 22, 1985
[87] PCT Pub. No.: WO85/04485
PCT Pub. Date: Oct. 10, 1985

[30] Foreign Application Priority Data
Mar. 26, 1984 [FR] France ............................ 84 04659

[51] Int. Cl.[4] ............................................. G01N 29/04
[52] U.S. Cl. ................................................... 73/636
[58] Field of Search ............... 73/636, 628, 641, 624, 73/614

[56] References Cited

U.S. PATENT DOCUMENTS

| | | | |
|---|---|---|---|
| 2,893,239 | 7/1959 | Renaut | 73/624 |
| 4,457,178 | 7/1984 | Turbe et al. | 73/636 |
| 4,487,071 | 12/1984 | Pagano et al. | 73/636 |
| 4,594,897 | 6/1986 | Bantz | 73/643 |

FOREIGN PATENT DOCUMENTS 216352  7/1968  U.S.S.R. ............................ 73/636

*Primary Examiner*—Stewart J. Levy
*Assistant Examiner*—John E. Chapman, Jr.
*Attorney, Agent, or Firm*—Sughrue, Mion, Zinn, Macpeak and Seas

[57] ABSTRACT

Apparatus for the inspection of track rails. The device comprises a truck (4) capable of displacement on the track, and comprises at least two ultrasound emitter and/or receiver probes (V, $O_1$, $O_2$) emitting in different directions, applied against the rolling plane of the rail (1) and at least an ultrasound prove (SA) provided at the vicinity of the rail, laterally offset, emitting an ultrasound beam to the side of the rail web. Application particularly to the detection and recognition of rail fish-plates.

6 Claims, 3 Drawing Figures

FIG_1
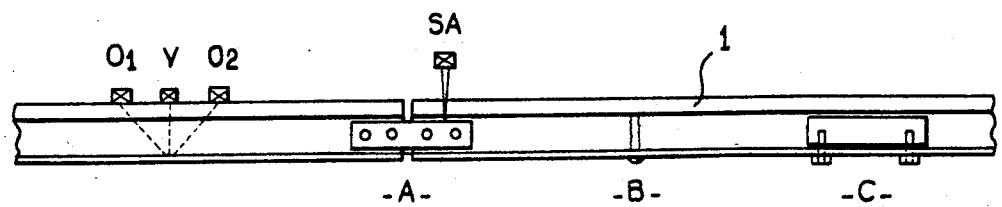
FIG_2
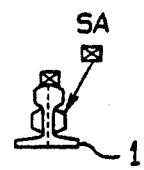
FIG_3
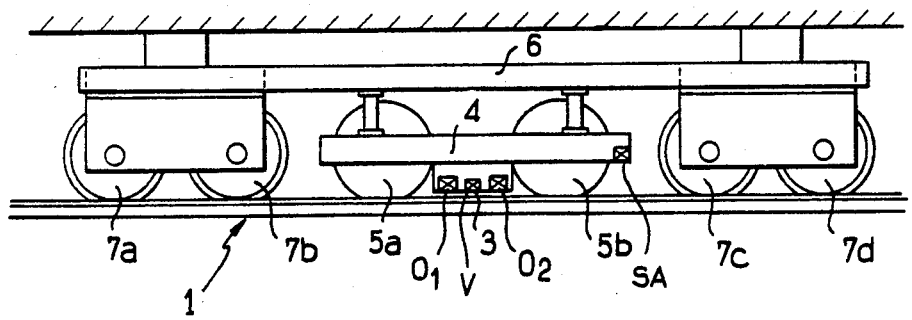

PROCESS AND DEVICE FOR THE AUTOMATIC RECOGNITION AND DETECTION OF DISCONTINUITIES AND IRREGULARITIES IN THE RAILS OF RAILROAD TRACKS

BACKGROUND OF THE INVENTION

The invention relates to the inspection of the rails of railroad tracks, and more particularly to a process for the automatic recognition of discontinuities or irregularities and especially the fished joints of the rails of railroad tracks, as well as to a device for the implementation of such a process.

The stresses and dynamic overloads to which the track is subjected cause the development of internal faults in the rail, such as oval flaws, horizontal, transverse or longitudinal cracks, star-shaped cracks, etc.

It is important to be able to detect these faults on the track using a non-destructive method, in order to be able to change defective sections of rail in time while distinguishing as far as possible between faults and joints or other discontinuities that can occur in the rails.

The most widely used method of non-destructive testing of the internal state of rails on the track is the sounding of the rail by ultrasonics. This technique consists in placing in contact with the rail head transmitting, receiving or transmitting-receiving probes, the orientation of which is adapted to the type of fault being looked for.

In general, light instruments employed by an operator or heavy instruments carried in rail cars are used.

In the first case, the operator sounds one or two lines of rail simultaneously using ultrasonic instruments adapted to this technique. A probe is placed in contact with the running surface of each rail. The operator advances slowly, at a speed of about 3 km/h, and checks all the ultrasonic detections on the screen of the instrument. He therefore has to analyse the results displayed by the instrument and correlate them with the rail. In fact not every ultrasonic detection is necessarily associated with an internal fault. For example the fishing holes in the rails appear very clearly on the instrument but must not be considered as faults. Another example is that relating to the detection of the ends of rails when these are fished. The rail, in this case, behaves like a rail with a vertical break through its full height. In this case the ultrasonic instrument indicates sounding anomalies. The operator can easily see the difference between a broken rail and the end of a rail when it is fished. He interprets the results of the ultrasonic sounding in order to sort certain data, helped by the fact that he can see the rail.

On the other hand, in the second case, when the detection equipment is carried in a sounding rail car, this analysis is made very difficult because of the speed at which the machine moves (which can be of the order of 30 to 50 km/h). It became necessary in this case to develop a process which enables the real faults in the rail to be distinguished from all the detections made by the instruments in order to sort the results automatically.

SUMMARY OF THE INVENTION

The purpose of the present invention is to enable the automatic detection and distinguishing of fished joints from the cracks present in the rails of railroad tracks by means of a detection equipment carried in a vehicle able to move at a relatively high speed.

The invention therefore relates to a process for the automatic detection and recognition of discontinuities and especially the fished joints of the rails of railroad tracks, on the track and continuously, by means of beams of ultrasonic waves, enabling the fished joints to be distinguished from the faults in the rail by carrying out an automatic sorting of the detection signals.

The invention also relates to a device for the implementation of such a process, able to be used on the track at relatively high speeds, in the order of 30 to 50 km/h.

More particularly, the process according to the invention enables the detection of any discontinuity or irregularity, and the automatic distinction between a fished joint connecting two rails, a welded and cracked joint, and a rail having a known fished fault.

The process according to the present invention, for the automatic recognition and detection of discontinuities and especially of fished joints in rails of railroad tracks, on the track and continuously, uses ultrasonic beams, and is distinguished in that at least two beams of different orientations are transmitted through the rail, and at least one beam of ultrasonic waves is transmitted in the air near to the web of the rail, and the received signals are compared.

According to a preferred implementation of the process of the invention, one of the two beams transmitted through the rail is perpendicular to the runnin surface of the rail while the other is oblique with respect to the axis of the rail. Both beams are transmitted in order to be reflected by the lower surface of the rail foot at approximately the same place.

The process of the invention is based on the fact that the received echoes are clearly differentiated according to the nature of the obstacle encountered by the beam of ultrasonic waves, i.e. a fished joint, a welded joint or a fished rail. In particular, the passing of an ultrasonic beam over a fishing hole causes specific and perfectly identifiable signals.

The following logic table is drawn up as a function of the two main data generally taken, which are the fishing holes in the web of the rail on the one hand, and the existing fishplates on the other hand.

|  | Fishing holes | Fishplates |
| --- | --- | --- |
| (A) Fished joint | yes | yes |
| (B) Welded joint | no (1) | yes |
|  | yes (2) | no |
| (C) Fished rail | no | yes |

(1) In the general case of electric welds
(2) In the case of thermit welds when the two rails have not been cut or changed The automatic discrimination of detections can be carried out starting with the result of this logic, as described in detail hereafter.

The reflections of the beam transmitted perpendicularly to the running surface of the rail are automatically differentiated by a selector which transmits a characteristic fishing hole V signal. In addition, any anomaly such as an internal fault, surface fault, orientation fault, fishing hole and interface between two fished rails causes an interruption in the obliquely transmitted beam, which results in a datum T transmitted by the receiving probe. Finally, when it encounters the upper edge of a fishplate, the ultrasonic beam transmitted in the air is reflected and the echo picked up by the probe causes the transmission of a signal SA by means of an electronic selector.

The logic definition of a fished joint is therefore given by: (SA.V.T).

The device according to the invention is adapted to the implementation of the above process. It comprises a truck carrying at least two transmitting and/or receiving ultrasonic probes transmitting in different directions applied against the running surface of the rail, and at least one ultrasonic probe located near the rail, laterally displaced, transmitting an ultrasonic beam towards the fillet of the rail web and the rail foot.

BRIEF DESCRIPTION OF THE DRAWINGS

The characteristics and advantages of the invention will appear in more detail in the following description, relating to a non-limiting preferred embodiment, with reference to the appended drawings which show:

in FIG. 1: a diagrammatic side showing the arrangement of the ultrasonic probes with respect to a fished rail.

in FIG. 2: an end view of the rail showing the positions of the probes with respect to the fishplate.

in FIG. 3: a diagrammatic view of a device according to the invention.

DETAILED DESCRIPTION OF THE PREFERRED EMBODIMENT

The length of rail (1) shown in FIG. 1 includes a fished joint (A), a welded joint (B) and a fished rail (C) which must be differentiated when sounded by the ultrasonic probes.

The device according to the invention, an example of which is shown in FIG. 3, comprises a probe-carrying truck (4) of usual type, capable of being pulled by a railroad vehicle. The truck carries several probes, V, $O_1$, $O_2$ and SA, whose positioning with respect to the rail (1) is clearly shown in FIGS. 1 and 2. Probes V, $O_1$ and $O_2$ are fixed to a support (3) that is integral with the truck (4) rolling on the rail (1) by means of rail wheels (5a) and (5b), and connected to the bogie (6) of a vehicle rolling by means of wheels (7a) to (7d). The position of the probe support is adjustable in height by known means. The truck (4) carries an ultrasonic transmitting-receiving probe V maintained by appropriate and known means in sound contact with the upper surface of the rail (1). This probe V transmits a high frequency beam of ultrasonic waves, perpendicular to the running surface of the rail, which passes through the rail head and the rail web and is reflected at the lower surface of the rail foot, perpendicularly to the rail foot, passes through the rail web and the rail head again and is picked up by the transmitting-receiving probe V. The ultrasonic beam is deflected when it encounters an obstacle such as a fault or a fishing hole in the rail. The reflections due to fishing holes are differentiated automatically by a selector which enables a sorting of the horizontally orientated faults and the fishing holes and transmits a specific fishing hole signal.

The truck (4) also carries two high frequency ultrasonic probes $O_1$ (transmitting) and $O_2$ (receiving) in sound contact with the rail, transmitting waves in the longitudinal plane of the rail in oblique directions. The waves transmitted by probe $O_1$ are reflected at non-zero incidence at the lower surface of the rail and are picked up by the receiving probe $O_2$. The two probes $O_1$ and $O_2$ are arranged on either side of the probe V. Any anomaly such as an internal fault, a surface fault, of any orientation, as well as the fishing holes and the interface between two fished rails results in an interruption in the reception of the wave by the receiving probe $O_2$.

Finally, the device includes a fourth transmitting-receiving probe SA transmitting a low frequency ultrasonic beam in the air towards the fishplate (A) present on each side of the rail web under the rail head. The wave is reflected by the upper edge of the fishplate, and the reflected wave is picked up by the receiving section of the probe SA which is connected to an electronic selector which generates a signal SA each time the probe picks up an echo.

As shown in FIGS. 2 and 3, probe SA is not in contact with the rail but is located above it in a position that is laterally displaced with respect to its longitudinal axis.

Probes V, $O_1$ and $O_2$ are of course maintained on the rail and in its longitudinal plane by appropriate means of known type.

According to the process of the invention, when the truck moves over the rails of the railroad track, the high frequency ultrasonic probes V, $O_1$ and $O_2$ transmit an ultrasonic beam through the rail while the low frequency probe SA transmits a wave in the air in the direction of the fillet of the rail web and the rail foot where the fishplate is fixed if necessary.

When a fished joint (A) occurs in the path of the moving truck, including both fishing holes and a fishplate on the rail web, the selector of the probe V transmits a signal V resulting from the reflection of the ultrasonic waves at the fishing holes. The beam transmitted by probe $O_1$ is deflected by the interface between the ends of the two fished rails, and the reception of the ultrasonic wave by probe $O_2$ is interrupted causing the transmission of a signal T. Finally, the transmitting-receiving probe SA receives an echo resulting from the reflection of the waves at the upper edge of the fishplate.

Thus the bringing together of the three signals V, T and SA, recorded by an appropriate electronic device, enables the detection of the fished joint.

On the other hand, on passing over a welded joint (B), probe SA does not record any echo and the fished joint detection device is therefore not activated. Similarly, on passing over a fished rail, the fishplate returns an echo to probe SA but the ultrasonic beam transmitted by probe $O_1$ is not deflected and the signal T is therefore not transmitted.

The spacing between the positions of the probes on the truck is of course automatically corrected by a known technique during the exploitation of the signals.

I claim:

1. In a process for the automatic in situ detection and recognition of discontinuities or irregularities in the rails of railroad tracks, on the track and continuously, using beams of ultrasonic waves, wherein at least two beams of different orientations are transmitted through the rail and received reflections thereof are compared, the improvement comprising: transmitting at least one further beam of ultrasonic waves through the air and towards the side of the web of the rail, and comparing the received reflections of the beams transmitted through the rail with received reflections of said further beam transmitted through the air to enable the distinguishing of cracks from fished joints along the rail.

2. Process as claimed in claim 1, wherein one of the two beams transmitted through the rail is perpendicular to the running surface of the rail while the other is oblique with respect to the axis of the rail.

3. Process as claimed in claim 2, wherein the two beams are reflected by the lower surface of the rail foot at approximately the same place.

4. In a device for the automatic in situ detection and recognition of discontinuities or irregularities in the rails of a railroad tracks, on the track and continuously, including a truck (4) capable of moving on the track and carrying at least two ultrasonic transmitting and/or receiving probes (V, $O_1$, $O_2$) transmitting beams in different directions and applied against the running surface of the rail (1), and means for comparing received reflections of said beams, the improvement comprising: at least one further ultrasonic probe (SA) located near the rail, laterally displaced, for transmitting a further ultrasonic beam through the air and towards the side of the rail web, and means for comparing the received reflections of the beams transmitted by the probes applied against the surface of the rail with received reflections of said further beam transmitted through the air to enable the distinguishing of cracks from fished joints along the rail.

5. Device as claimed in claim 4, wherein a transmitting probe ($O_1$) transmitting an oblique beam and an associated receiving probe ($O_2$) are arranged on either side of a central probe (V) transmitting perpendicularly to the running surface of the rail (1).

6. Device as claimed in claim 5, wherein the further prove (SA) is a transmitting-receiving probe transmitting in the air a low frequency ultrasonic beam directed towards the fillet of the rail web and the rail foot.

* * * * *